(12) United States Patent
Kong et al.

(10) Patent No.: US 11,974,982 B2
(45) Date of Patent: May 7, 2024

(54) STIMULUS-RESPONSIVE ANTIOXIDANT CRYSTALS AND METHOD FOR THEIR PREPARATION

(71) Applicant: The Board of Trustees of the University of Illinois, Urbana, IL (US)

(72) Inventors: Hyunjoon Kong, Champaign, IL (US); Byoungsoo Kim, Urbana, IL (US); Jonghwi Lee, Seoul (KR); Youngjun Kim, Saarbrucken (DE); Ryan Cree Miller, Champaign, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 23 days.

(21) Appl. No.: 17/217,524

(22) Filed: Mar. 30, 2021

(65) Prior Publication Data
US 2021/0308100 A1    Oct. 7, 2021

Related U.S. Application Data

(60) Provisional application No. 63/004,549, filed on Apr. 3, 2020.

(51) Int. Cl.
| | |
|---|---|
| A61K 31/375 | (2006.01) |
| A61K 31/198 | (2006.01) |
| A61K 31/353 | (2006.01) |
| A61K 47/18 | (2017.01) |
| A61K 47/24 | (2006.01) |
| A61K 47/59 | (2017.01) |
| A61K 47/61 | (2017.01) |

(52) U.S. Cl.
CPC .......... *A61K 31/375* (2013.01); *A61K 31/198* (2013.01); *A61K 31/353* (2013.01); *A61K 47/18* (2013.01); *A61K 47/24* (2013.01); *A61K 47/59* (2017.08); *A61K 47/61* (2017.08)

(58) Field of Classification Search
CPC .. A61K 31/375; A61K 31/198; A61K 31/353; A61K 47/18; A61K 47/24; A61K 47/59; A61K 47/61; A61K 47/34; A61K 9/146
See application file for complete search history.

(56) References Cited

U.S. PATENT DOCUMENTS 4,515,804 A     5/1985 Marti
6,048,736 A  *  4/2000 Kosak ................. A61K 9/5192
                                                    436/536

FOREIGN PATENT DOCUMENTS

KR          102047173 B1  *  11/2019

OTHER PUBLICATIONS

Kim et al (Small, 2019, 15, 1900765) (Year: 2019).*
Neto et al. (Small, 2014, 10, No. 12, 2459-2469) (Year: 2014).*
Huo (Polm. Chem. 2014, 5, 1519-1528) (Year: 2014).*
Chen et al (Molecules 2018, 23, 1179) (Year: 2018).*
Yang (Chinese Chemical Letters, 28, 2017, 2099-2104) (Year: 2017).*
AI translated KR102047173B1 from Korean Patent Database (Year: 2019).*
AI translated KR102047173B1 from ESPACENET (Year: 2019).*
Zhong et al., "Dissolution Behavior of the Crystalline Inclusion Complex Formed by the Drug Diflunisal and Poly(e-caprolactone)", Crys. Growth Des. 2017, 17, 355-362.
Deng et al., "Serum-resistant, reactive oxygen species (ROS)-potentiated gene delivery in cancer cells mediated by fluorinated, diselenide-crosslinked polyplexes", Biomater. Sci., 2017, 5, 1174.
Xu et al., "Reactive Oxygen Species (ROS) Responsive Polymers for Biomedical Applications", Macromolecular Bioscience, Feb. 2016, 13 pages.

* cited by examiner

*Primary Examiner* — Jeffrey H Murray
*Assistant Examiner* — Luisalberto Gonzalez
(74) *Attorney, Agent, or Firm* — Dilworth IP, LLC

(57) ABSTRACT

Compositions comprising an active oxygen-responsive antioxidant crystal, methods of making them, and methods for controlling the dissolution rate and/or altering the crystallization behavior of an antioxidant are disclosed. The crystals comprise an antioxidant and a disulfide- or diselenide-crosslinked polymer that is adsorbed onto a surface of the antioxidant. Upon exposure to an active-oxygen stimulus, the polymer de-crosslinks to release the antioxidant from the composition in an amount effective to counteract the stimulus. While prior approaches to altering dissolution rates have relied on passive zero- or first-order kinetics that are independent of ROS levels, the inventive compositions actively respond by releasing antioxidant in an amount proportional to the concentration of active-oxygen species present. The crystallization methods are simple and scalable. The antioxidant balances ROS concentration and allows formulators of nutritional supplements, drug therapies, and other applications to more effectively use antioxidants while avoiding undesirable levels of antioxidative stress.

20 Claims, 7 Drawing Sheets

STIMULUS-RESPONSIVE ANTIOXIDANT CRYSTALS AND METHOD FOR THEIR PREPARATION

FIELD OF THE INVENTION

The invention relates to stimulus-responsive antioxidant crystals and methods for making them.

BACKGROUND OF THE INVENTION

Reactive oxygen species (ROS), which include superoxide anions, hydroxyl radicals, and hydrogen peroxide, are by-products of cellular metabolism. Normally, ROS function as signaling molecules that regulate adhesion, proliferation, differentiation, senescence, and apoptosis. However, abnormal overproduction of ROS and/or prolonged free-radical action increases oxidative stress and can overwhelm a cell's ability to maintain homeostasis. The increased oxidative stress denatures protein, DNA, and is cells.

Exogenous antioxidants (e.g., ascorbic acid, N-acetylcysteine, polyphenols) are administered either to scavenge overproduced ROS in tissue or to stimulate cells to produce anti-oxidizing enzymes (e.g., superoxide dismutase, glutathione peroxidase). However, fast dissolution and rapid metabolism of most antioxidants stimulate cells to overproduce antioxidant enzymes and cause undesirable antioxidative stress. Ideally, ROS levels are balanced by controlling the dissolution rate of antioxidants.

The pharmaceutical industry relies on crystallization to influence the solubility, bioavailability, and stability of drugs. Various salts and polymers introduced during crystallization can impact nucleation and growth behavior at different degrees of supersaturation thereby producing crystallized forms having dramatically different dissolution profiles, stability, and efficacy when compared with pure drug crystals.

Usually, recrystallized drugs in physiological media exhibit a passive-release profile characterized by zero- or first-order kinetics. Too often, the dissolved amount of antioxidant exceeds the amount needed, the antioxidative stress level of the cell is increased, and cell growth is limited. Ideally, the antioxidant crystal could sense the ROS level and actively tune the dissolution rate.

Recently, Q. Deng et al. (*Biomater. Sci.* 5 (2017) 1174) described serum-resistant ROS-potentiated gene delivery in cancer cells mediated by fluorinated diselenide-crosslinked polyplexes. As part of this work, polyethylenimines were reacted with a diselane diacrylate crosslinker to produce an ROS-responsive diselenide-PEI. Z. Zhong et al. (*Cryst. Growth Des.* 17 (2017) 355) describe inclusion complexes made from drugs and polycaprolactone to modulate and optimize dissolution behavior. Such compositions offer alternatives to crystalline polymorphs, but they exhibit a passive-release profile that is not responsive to oxidative stimuli or other signaling molecules. Q. Xu et al. (*Macromol. Biosci.* 16 (2016) 635) review recent developments in making various ROS-responsive polymers for biomedical applications, including polymeric nanomaterials and macroscopic polymeric scaffolds and hydrogels. Methods for crystallizing drugs or controlling dissolution rates of antioxidant crystals are not disclosed. U.S. Pat. No. 4,515,804 describes polymorphs and stability of a recrystallized antioxidant (catechin) but no effort is made to control the dissolution rate of the crystals.

The industry would benefit from the availability of a simple, effective way to modify the bioavailability, therapeutic efficacy, and stability of crystalline drugs, especially antioxidants. We wondered whether polymer-directed recrystallization could be used to generate stimulus-responsive antioxidants.

SUMMARY OF THE INVENTION

In one aspect, the invention relates to a composition comprising an active oxygen-responsive antioxidant crystal. The crystal comprises an antioxidant and a disulfide- or diselenide-crosslinked polymer that is adsorbed onto a surface of the antioxidant. Upon exposure to an active-oxygen stimulus, the polymer de-crosslinks to release the antioxidant from the composition in an amount effective to counteract the stimulus.

The invention includes methods of making the compositions described above. One such method comprises crystallizing an antioxidant in the presence of a disulfide- or diselenide-crosslinked polymer wherein at least a portion of the polymer is adsorbed onto a surface of the antioxidant. Upon exposure to an active-oxygen stimulus, the polymer can de-crosslink to release the antioxidant from the composition in an amount effective to counteract the stimulus.

In another aspect, the invention relates to a method which comprises controlling the dissolution rate and/or altering the crystallization behavior of a water-soluble antioxidant. In this method, the antioxidant is crystallized in water in the presence of a disulfide- or diselenide-crosslinked polymer to produce a crystallized composition. At least a portion of the polymer is adsorbed onto a surface of the antioxidant.

We found that polymer-directed recrystallization can be used to generate stimulus-responsive antioxidants. While prior approaches to altering dissolution rates of drugs, including antioxidants, have relied on passive zero- or first-order kinetics that are independent of ROS levels, the inventive compositions actively respond by releasing antioxidant in an amount proportional to the concentration of active-oxygen species present. The antioxidant balances ROS concentration without the need for nanoparticles, hydrogels, or toxic chemicals. The crystallization methods are simple and scalable. Formulators of nutritional supplements, drug therapies, food additives, beverages, cosmetics, rubber, plastics, and other applications can more effectively use antioxidants while avoiding, for many applications, undesirable levels of antioxidative stress.

DETAILED DESCRIPTION OF THE INVENTION

Figure 1:
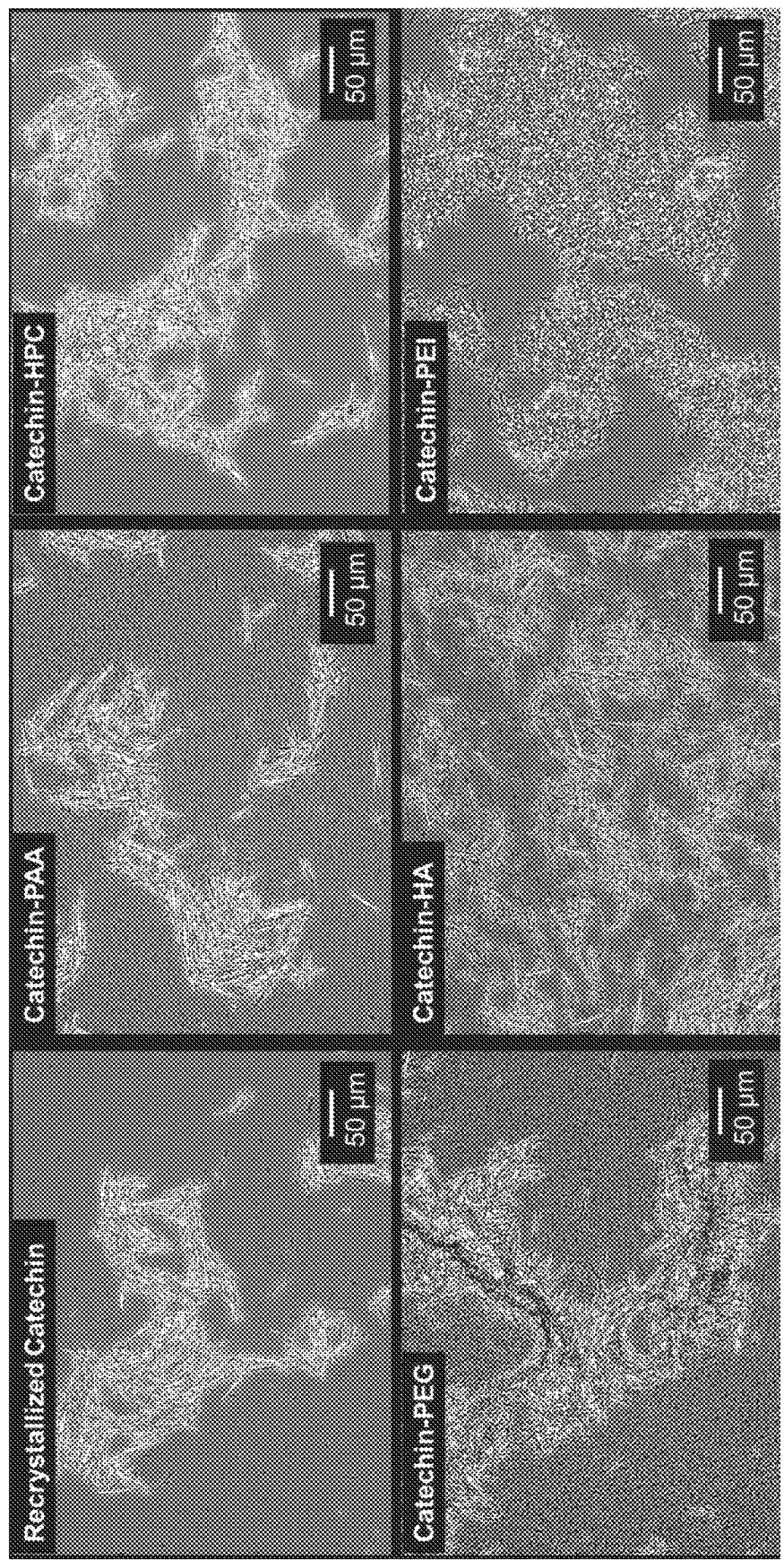
FIG. 1 shows a series of optical micrographs of catechin crystals formed with or without various polymer additives.

In one aspect, the invention relates to a composition comprising an active oxygen-responsive antioxidant crystal. The crystals comprise an antioxidant and a disulfide- or diselenide-crosslinked polymer that is adsorbed onto a surface of the antioxidant. Upon exposure to an active-oxygen stimulus, the polymer de-crosslinks to release the antioxidant from the composition in an amount effective to counteract the stimulus.

The Antioxidant

Antioxidants suitable for use in making the active oxygen-responsive antioxidant crystals are natural or synthetic antioxidants. Natural antioxidants occur in fruits, vegetables, plants, seeds, and other sources.

Natural antioxidants include, among others, phenolics, carotenoids, and vitamins. Phenolics (or polyphenols) include phenolic acids and their esters (e.g., cinnamic acid derivatives such as p-coumaric, ferulic, ellagic, or caffeic acids; benzoic acid derivatives such as gallic acid or hydroxybenzoic acids), flavonoids (e.g., flavonols, flavonones, catechins, flavones, anthocyanidins, and isoflavonoids), stilbenes (e.g., resveratrol or pterostilbene), and lignans. Flavones include, e.g., apigenin, luteolin, and tangertin. Flavonols include, for example, isorhamnetin, kaempferol, myrcetin, condensed tannins, and quercetin. Flavonones include, for example, eriodictyol, hesperetin, and naringenin. Anthocyanidins include, for example, cyanidin, delphinidin, malvidin, pelargonidin, peonidin, and petunidin.

Vitamins include L-ascorbic acid (vitamin C), vitamin A, vitamin E, and related compound classes, including chromans, tocopherols, tocotrienols, and the like.

Carotenoids include beta-carotene, alpha-carotene, lycopene, lutein, zeaxanthin, and the like.

Other natural antioxidants include N-acetylcysteine, glutathione, coenzyme Q10, melatonin, erythorbic acid (D-ascorbic acid), and lipoic acid.

Synthetic antioxidants are used in foods, supplements, cosmetics, synthetic rubber, plastics, and other applications. Examples include, among others, butylated hydroxytoluene (BHA), butylated hydroxyanisole (BHA), EDTA, ethoxyquin, propyl gallate, octyl gallate, dodecyl gallate, and t-butylhydroxyquinone (TBHQ).

The antioxidant can be water-soluble or oil-soluble. In preferred aspects, the antioxidant is water-soluble. By "water-soluble," we mean that an aqueous solution containing at least 3 wt. %, or preferably at least 5 or 10 wt. %, of the antioxidant can be made.

The disulfide- or diselenide-crosslinked polymer

A wide variety of natural or synthetic polymers can be modified to incorporate a disulfide or diselenide linkage. In some aspects, the polymer is water-soluble. Suitable polymers include, for example, polyethylenimines, polyethylene glycols, polyglucosides, polysaccharides, hyaluronic acid polysaccharides, dopamine conjugates of polysaccharides, polyglycerols, hydroxyalkylcelluloses, polyvinyl acetates, polyvinyl alcohols, acrylic polymers, polyacrylamides, N-vinylpyrrolidone polymers, block copolymers thereof, and the like, and mixtures thereof.

In some aspects, the polymer is a diselenide-crosslinked, linear or branched polyethylenimine. In a preferred aspect, the polymer is a diselenide-crosslinked, branched polyethylenimine and the antioxidant is catechin.

In another preferred aspect, the polymer is a diselenide-crosslinked hyaluronic acid grafted with dopamine (HA-DOPA) and the antioxidant is N-acetylcysteine.

Methods for making the disulfide- or diselenide-crosslinked polymers are known in the art. See, e.g., Q. Deng et al. (*Biomater. Sci.* 5 (2017) 1174). One synthetic method shown below in the experimental section generates a diselenide-crosslinked polyethylenimine by conjugate addition of the PEI to a diselenide-functional diacrylate. In another example, hyaluronic acid, which has carboxylate functionality, is amidated with a diselenide-functional diamine. The skilled person understands how to react polymers with carboxylic acid or ester functionality with dihydroxy- or diamine-functional disulfides or diselenides to produce suitable disulfide- or diselenide-crosslinked polymers. Similarly, diamine-functional disulfides or diselenides can be reacted with diacrylates or other polymers terminated with activated carbon-carbon double bonds by conjugate addition (i.e., "Michael" addition) to produce the disulfide- or diselenide-crosslinked polymers.

Generally, diselenide-crosslinked polymers will be more responsive to an active-oxygen stimulus because the bond energy of the Se-Se bond is only about 175 kJ/mol, compared with about 213 kJ/mol for a disulfide bond. Depending on the application and the desired degree of responsiveness to an active-oxygen stimulus, a polymer having either of the S-S or Se-Se linkages might be preferred. In some aspects, it may be desirable to use a polymer having both S-S and Se-Se linkages, or to use a combination of different polymers having S-S, Se-Se, or both functionalities.

The amount of disulfide- or diselenide-crosslinked polymer relative to the amount is of antioxidant needed for a particular application will depend on nature of the polymer, the kind of antioxidant, the intended use, the desired release profile, and many other factors within the skilled person's discretion. In some aspects, the active oxygen-responsive antioxidant crystals comprise 1 to 20 wt.%, or 2 to 10 wt.%, or 3 to 8 wt.%, of the disulfide- or diselenide-crosslinked polymer based on the combined amounts of antioxidant and disulfide- or diselenide-crosslinked polymer.

The Active-Oxygen Stimulus

The active-oxygen stimulus can be any source of hydroxy radicals, hydrogen peroxide, superoxide anions, hypochlorous acid, peroxynitrite, or a singlet oxygen-containing species. The particular variety of active-oxygen stimulus generally occurs naturally, especially in the cells of humans and other living organisms, and depends on the environment in which the active oxygen-responsive antioxidant crystal will be used.

De-Crosslinking to Release Antioxidant

Upon exposure to an active-oxygen stimulus, the polymer de-crosslinks to release the antioxidant from the crystal in an amount effective to counteract the stimulus. De-crosslinking occurs when a S-S or a Se-Se bond present in the polymer ruptures in response to a reaction with an active-oxygen species. When the S-S or Se-Se bond breaks, antioxidant is released and becomes available to quench or counteract the free-radical species. The compositions are well-suited to respond proportionally to the presence of active oxygen. The disulfide- or diselenide-functional polymer allows the crystals to modulate their dissolution rate in response to the localized ROS level: the greater the exposure to an active-oxygen species, the more the antioxidant will be released. Conversely, when the level of active-oxygen species is low or absent, the antioxidant crystal can remain intact or be released at a slower dissolution rate. The "stimulus-responsive" nature of the inventive compositions distinguishes them from prior compositions in which a drug is crystallized with a polymer, a salt, or some other additive to alter its solubility and dissolution profile. In that case, the dissolution is passive and follows zero- or first-order kinetics rather than actively responding to a stimulus. Consequently, the inventive compositions can avoid releasing too much of the antioxidant is before it is needed and thereby circumvent undesirable antioxidative stress.

Methods

The invention includes methods of making active oxygen-responsive antioxidant crystals. One of such methods comprises crystallizing an antioxidant in the presence of a disulfide- or diselenide-crosslinked polymer to produce a composition comprising an active oxygen-responsive antioxidant crystal. At least a portion of the polymer is adsorbed onto a surface of the antioxidant. Upon exposure to an active-oxygen stimulus, the polymer can de-crosslink to release the antioxidant from the composition in an amount effective to counteract the stimulus. In some aspects, the antioxidant, the polymer, or both are water-soluble. Suitable antioxidants and polymers have already been described. In some aspects, it is desirable to crystallize the antioxidant and the disulfide- or diselenide-crosslinked polymer in the presence of a buffer solution, such as phosphate-buffered saline (PBS).

Another method comprises controlling the dissolution rate, altering the crystallization behavior, or both, of a water-soluble antioxidant. In this method, the antioxidant is crystallized in water in the presence of a disulfide- or diselenide-crosslinked polymer to produce a crystallized composition. At least a portion of the polymer is adsorbed onto a surface of the antioxidant. In some aspects, upon exposure of the composition to an active-oxygen stimulus, the polymer can de-crosslink to release the antioxidant from the composition in an amount effective to counteract the stimulus.

The following examples merely illustrate the invention; the skilled person will recognize many variations that are within the spirit of the invention and scope of the claims.

Synthesis of PEI Crosslinked with ROS-Responsive Diselenide

The method of Q. Deng et al. (*Biomater. Sci.* 5 (2017) 1174) is generally used to prepare diselanediylbis(ethane-2, 1-diyl)diacrylate. Thus, disodium diselenide is reacted with an equivalent of 2-bromoethanol to give bis(2-hydroxyethyl)diselenide. Reaction of the diol with acryloyl chloride provides the desired diacrylate crosslinker. The diacrylate is then reacted with a branched polyethylenimine to generate an ROS-responsive PEI-diselenide. Details appear below.

2,2-Diselanediylbis(ethan-1-ol)

Sodium borohydride (2.27 g, 0.06 mol) is dissolved in deionized water (50 mL) under nitrogen. Selenium (2.4 g, 0.03 mol) is added to the mixture in batches at 25° C. with stirring. After the mixture becomes milky white, more selenium (2.4 g, 0.03 mol) is added. The mixture is held at 80° C. for 3 h, then cooled to room temperature. 2-Bromoethanol (7.87 g, 0.03 mol) in THF (100 mL) is added dropwise, and then the mixture is refluxed for 24 h. The product is extracted with dichloromethane (3×100 mL). The organic portions are combined, washed with 1 N aq. NaCl and water, and then dried (MgSO$_4$). The crude product is concentrated, then purified by column chromatography on silica gel (EtOAc/n-hexane, 1/1 by vol.). The expected diol product is obtained as a yellow oil (60%). $^1$H NMR (500 MHz, CDCl$_3$) δ (ppm): 4.01-3.98 (t, 1H), 3.93-3.91 (t, 4H), 3.31-3.28 (t, 1H), 3.12-3.09 (t, 4H). $^{13}$C NMR (500 MHz, CDCl$_3$) δ (ppm): 61.7, 32.7.

Diselanediylbis(ethane-2,1-diyl)diacrylate 2,2'-Diselanediylbis(ethan-1-ol) (2.5 g, 10 mmol, 1 equiv.) is dissolved in dichloromethane (20 mL) containing triethylamine (4.45 g, 50 mmol, 5 equiv.) at 0° C. Acryloyl chloride (2.45 mL, 30 mmol, 3 equiv.) is added dropwise to the mixture, which is then stirred overnight. The reaction product is extracted with dichloromethane. The organic extracts are combined, washed with 1N NaCl and water, and then dried (MgSO$_4$). Column chromatography on silica gel (EtOAc/n-hexane, 1/1 by vol.) provides the diacrylate as a yellow oil (48%). $^1$H NMR (500 MHz, CDCl$_3$) δ (ppm): 6.44-6.38 (d, 4H), 6.15-6.07 (dd, 4H), 5.87-5.81 (d, 4H), 4.47-4.41 (t, 4H), 3.20-3.10 (t, 4H). $^{13}$C NMR (500 MHz, CDCl$_3$) δ (ppm): 165.8, 131.2, 128.1, 64.1, 27.3.

Hyaluronate-Dopamine Synthesis

Hyaluronate-dopamine (HA-DOPA) is synthesized using carbodiimide chemistry. In a 250-mL round-bottom flask, 250 mg of sodium hyaluronate ($M_n$=900 kDa) is is dissolved in 2-(N-morpholino)ethanesulfonic acid ("MES") buffer (pH=6.5). Once fully dissolved, 1-ethyl-3-(3-dimethylaminopropyl)carbodiimide hydrochloride ("EDC," 59.4 mg) and N-hydroxysulfosuccinimide ("sulfo-NHS," 67.3 mg) are dissolved in the HA solution for 15 min. Dopamine hydrochloride (29.4 mg) is then dissolved in the solution, and the reaction is allowed to proceed for 12 h. The resulting product is dialyzed (molecular weight cut-off: 12-14 kDa) against deionized water for 2 days with water changes twice a day. Following purification, the product is lyophilized and stored at −4° C. The degree of dopamine substitution to HA is determined using $^1$H-NMR to characterize the molar fraction of conjugated carboxylic acid groups. Degree of dopamine substitution: 24.7%.

PEI crosslinked with diselenide

The number of crosslinks is controlled by adjusting the molar ratio of PEI to diselanediylbis(ethane-2,1-diyl)diacrylate to values from 1:1 to 1:5. PEI and the diacrylate are dissolved in N,N-dimethylformamide and stirred at 60° C. for 48 h. The mixture is dialyzed against deionized water using a dialysis tube (MWCO=3.5 kDa) for 2 days and then lyophilized. The average molecular weight of resulting PEI-diselenide is examined by gel-permeation chromatography.

Preparation of catechin crystals by polymer-directed recrystallization

A series of polymer additives (30 mg, 10 wt.% based on the amount of catechin used) are dissolved in deionized water (9.3 mL) for 1 day at 40° C. to ensure complete dissolution. The polymers evaluated are: a branched polyethylenimine ("PEI," $M_w$=1800 g/mol, Sigma-Aldrich); poly(acrylic acid) ("PAA," $M_w$=1800 g/mol, Sigma-Aldrich); hydroxypropyl cellulose ("HPC," $M_w$=40,000 g/mol, Sigma-Aldrich); polyethylene glycol ("PEG," 950-1050 g/mol, Sigma-Aldrich); hyaluronic acid ("HA," $M_w$=620-1200 g/mol, Kikkoman). Catechin hydrate (0.30 g) is then added, and the mixtures are stirred until solids are completely dissolved. The mixtures are cooled to 20° C. with a controlled cooling rate of 1° C/min, and the solutions are further kept for 24 h until light-orange crystals form. The mixtures are filtered through a polyvinylidene fluoride membrane is (HVLP04700, pore size: 0.45 µm, Millipore) to isolate catechin crystals, which are then gently washed with water to remove any unbound polymer and dried under vacuum at room temperature for 24 h.

Characterization

Optical microscopy

The morphology of catechin crystals is examined with an optical microscope (Leica DMIL) and an environmental scanning electron microscope (ESEM, Quanta FEG 450, FEI) at 10 kV acceleration voltage. One hundred particles from ten different SEM images of each sample are analyzed to measure the average particle size and aspect ratio.

Figure 2:
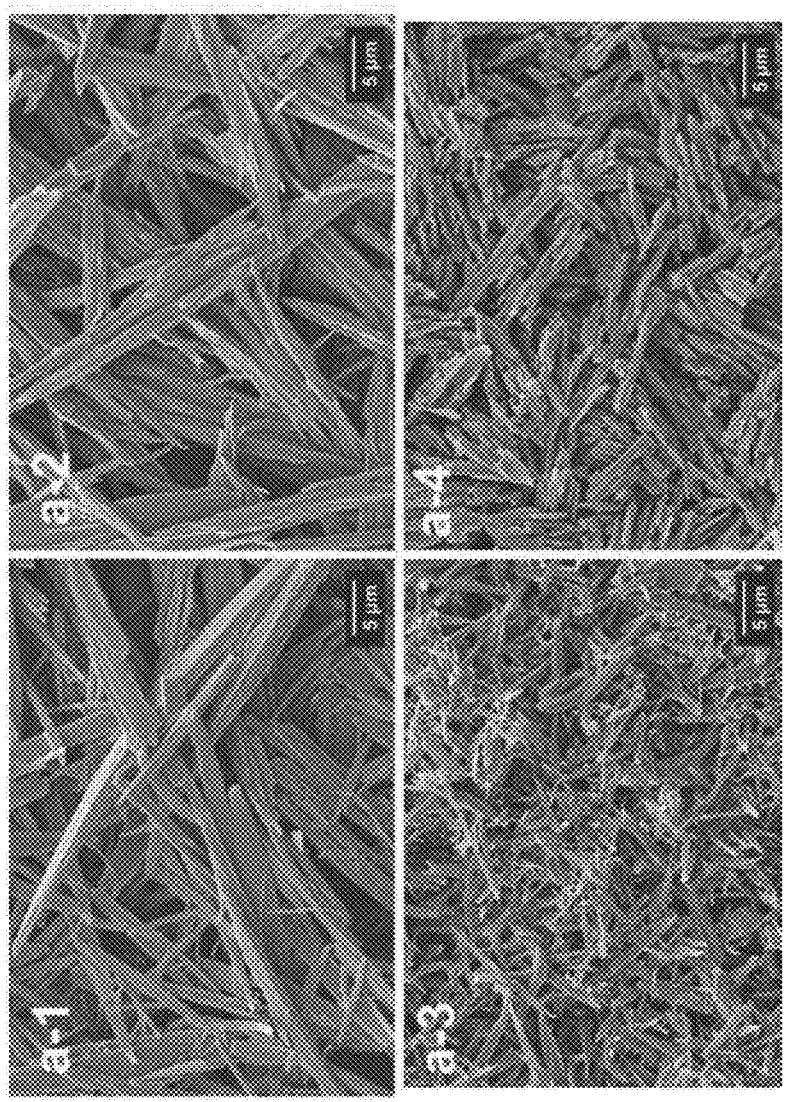
FIG. 2 shows scanning electron micrographs of pure catechin crystals, catechin recrystallized with polyethylenimine (PEI), or catechin recrystallized with a PEI that is crosslinked with diselenide ("PEI-diselenide").

Micrographs of the recrystallized catechin samples show that catechin alone provides needles having an average diameter and length, respectively, of 2.2 and 35.2 µm (see FIG. 1, top left image and FIG. 2, a-1). When the polymer is PAA, HPC, PEG, or HA, the micrographs in FIGS. 1 and 2 show that the size and shape of the catechin crystals are essentially unchanged when compared with recrystallized catechin alone. FIG. 2, a-2 shows the image for the catechin crystallized in the presence of hyaluronic acid (HA). In contrast, when the polymer is PEI (FIG. 1, bottom right image and FIG. 2, a-3), acicular needles having an average diameter and length, respectively, of 0.5 and 6.5 µm are produced. With the diselenide-PEI sample, results similar to the PEI sample are obtained. The results demonstrate that, among the polymers tested, only PEI can influence the morphology of the catechin crystals, and this influence is maintained when the PEI is crosslinked with the diselenide diacrylate.

Differential Scanning Calorimetry

The polymorphs of catechin crystals are investigated by differential scanning calorimetry (Perkin Elmer Diamond). Melting behavior is monitored under heating from 30° C. to 250° C. at 10° C/min.

Figure 3:
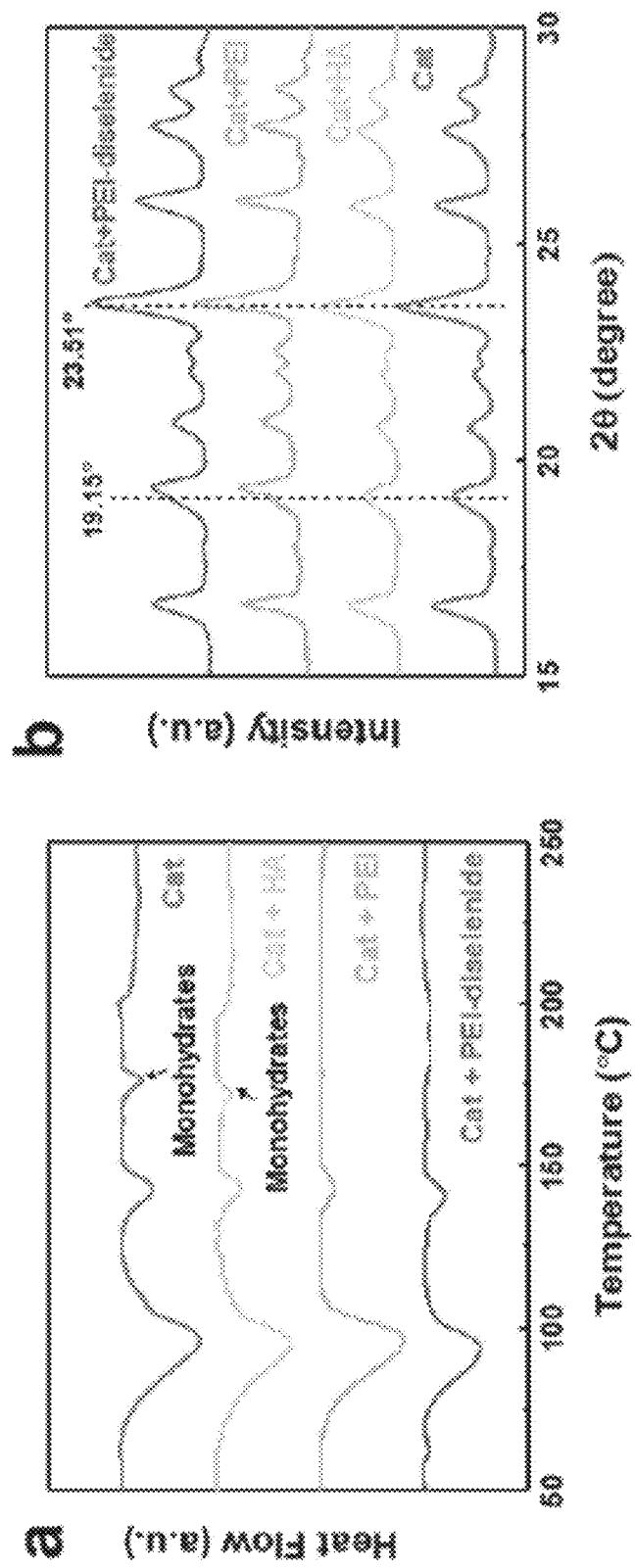
FIG. 3 shows differential scanning calorimetry thermograms (*a*) and X-ray diffraction patterns (*b*) obtained from a series of recrystallized catechins.

Results appear in FIG. 3(a). The melting point of the recrystallized drug indicates its crystalline form. There are seven microcrystalline forms of catechin, including two tetrahydrates and two monohydrates. The DSC thermogram of the recrystallized catechin (top trace) exhibits three main peaks at 96, 143 and 177° C. Melting points at 96 and 143° C. correspond to the tetrahydrates. Monohydrate forms of catechin have a melting point of 177° C. Catechin recrystallized in the presence of hyaluronic acid (FIG. 3(a), second trace from the top) shows similar melting points to the polymer-free catechin crystals, i.e., a mixture of tetra- and monohydrates. In contrast, DSC thermograms of the catechin recrystallized with PEI (FIG. 3(a), second trace from the bottom) or PEI-diselenide (Fig. 3(a), bottom trace) display only two transitions corresponding to the melting points of the tetrahydrates (i.e., 96 and 143° C.).

X-ray Diffraction

X-ray diffraction analysis (MiniFlex 600, Rigaku) is conducted to observe changes in the content of the crystal phases. The scans are performed in the range of 10 to 80 degrees 2θ at 10 degrees/min.

The X-ray diffraction patterns of the recrystallized catechin are consistent with the results of the DSC analysis. Catechin recrystallized in water and catechin recrystallized in the presence of hyaluronic acid (FIG. 3(b), bottom two traces) show peaks at 19.15° and 23.51°, which correspond to monohydrates. Both conditions also show multiple peaks corresponding to tetrahydrates (16.65°, 20.88°, 25.95°, and 27.7°). In contrast, catechins recrystallized with PEI or PEI-diselenide (FIG. 3(b), top two traces) exhibit peaks corresponding to tetrahydrates.

Isothermal Titration Calorimetry

Thermodynamic analysis of the association between catechin and polymer additives is performed by isothermal titration calorimetry (MicroCal). The 1.45-mL sample cell is filled with a 0.5 mM polymer solution. The cell is titrated with 28 injections of 10 µL of catechin solution (0.05 mM). Each injection is performed over 17.1 s with a delay of 300 s between injections while stirring at 300 rpm. Thermodynamic binding parameters such as the binding constant, the change in enthalpy, and the change in entropy are obtained and calculated by fitting data to a single-site binding model. The first data point is excluded.

In particular, we quantify the changes in the enthalpy (ΔH) and Gibbs free energy (ΔG) of the catechin solution when the polymers of interest are added to water at 40° C. is The change in entropy (ΔS) is back-calculated from the values of ΔH and ΔG at a given temperature (T) using the equation ΔS=(ΔH−ΔG)/T.

Figure 4:
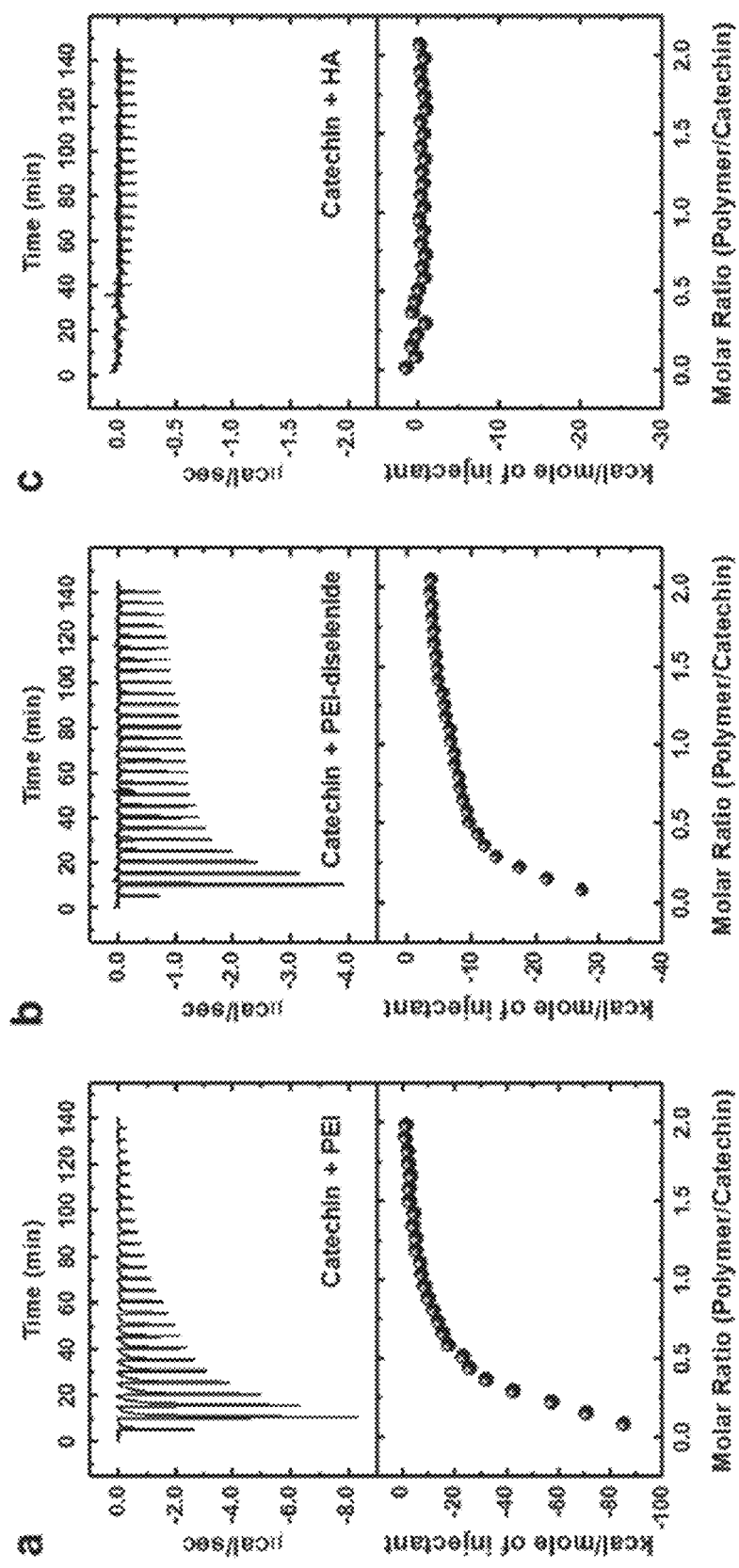
FIG. 4 shows representative calorimetric titration results from catechin solutions with (*a*) PEI, (*b*) PEI-diselenide, and (*c*) hyaluronic acid (HA).

The mixture of catechin and PEI shows exothermic thermograms with ΔH and ΔG of −55.6 and −7.2 kcal/mol, respectively (FIG. 4a and Table 1). This result affirms that the interaction between catechin and PEI is favorable thermodynamically. The negative, zo back-calculated ΔS (−1.2 kcal/mol) suggests that the exothermic interaction between catechin and PEI drives the thermodynamically favorable recrystallization process.

TABLE 1

| Thermodynamic parameters from ITC analysis | | | | |
|---|---|---|---|---|
| Polymer added | ΔH | ΔG | ΔS | ΔK |
| PEI | −55.82 | −7.15 | −1.21 | 9.71 |
| PEI-diselenide | −25.69 | −6.58 | −0.48 | 3.88 |
| Hyaluronic acid | −0.30 | −2.87 | 0.06 | 0.01 |

The mixture of catechin and PEI-diselenide exhibits the same levels of ΔH and ΔG as the mixture of catechin and PEI (FIG. 4b and Table 1). However, the binding constant (K) is almost 2.5-fold smaller than that for the mixture of catechin and PEI. The exothermic interaction between catechin and PEI-diselenide decreases with an increasing molar ratio of diselenide, possibly due to having fewer amine groups available for binding with catechin. In contrast, no significant heat changes are observed with the addition of hyaluronic acid to the catechin solution (FIG. 4c). Accordingly, the binding constant (K) is almost zero. The results indicate little interaction between hyaluronic acid and catechin.

Gel-Permeation Chromatography

The molecular weight and polydispersity of PEI-diselenide are determined by gel permeation chromatography (Breeze 2 GPC, Waters) with a Styragel HT column (Waters). A mixture of acetic acid (0.1 mol/L)/sodium acetate (0.1 mol/L) (pH 2.8) is used as the eluent. Elution rate: 1 mL/min. Polystyrene standards are used for calibration.

Analysis of the Release Profile of Catechin Crystals

Figure 5:
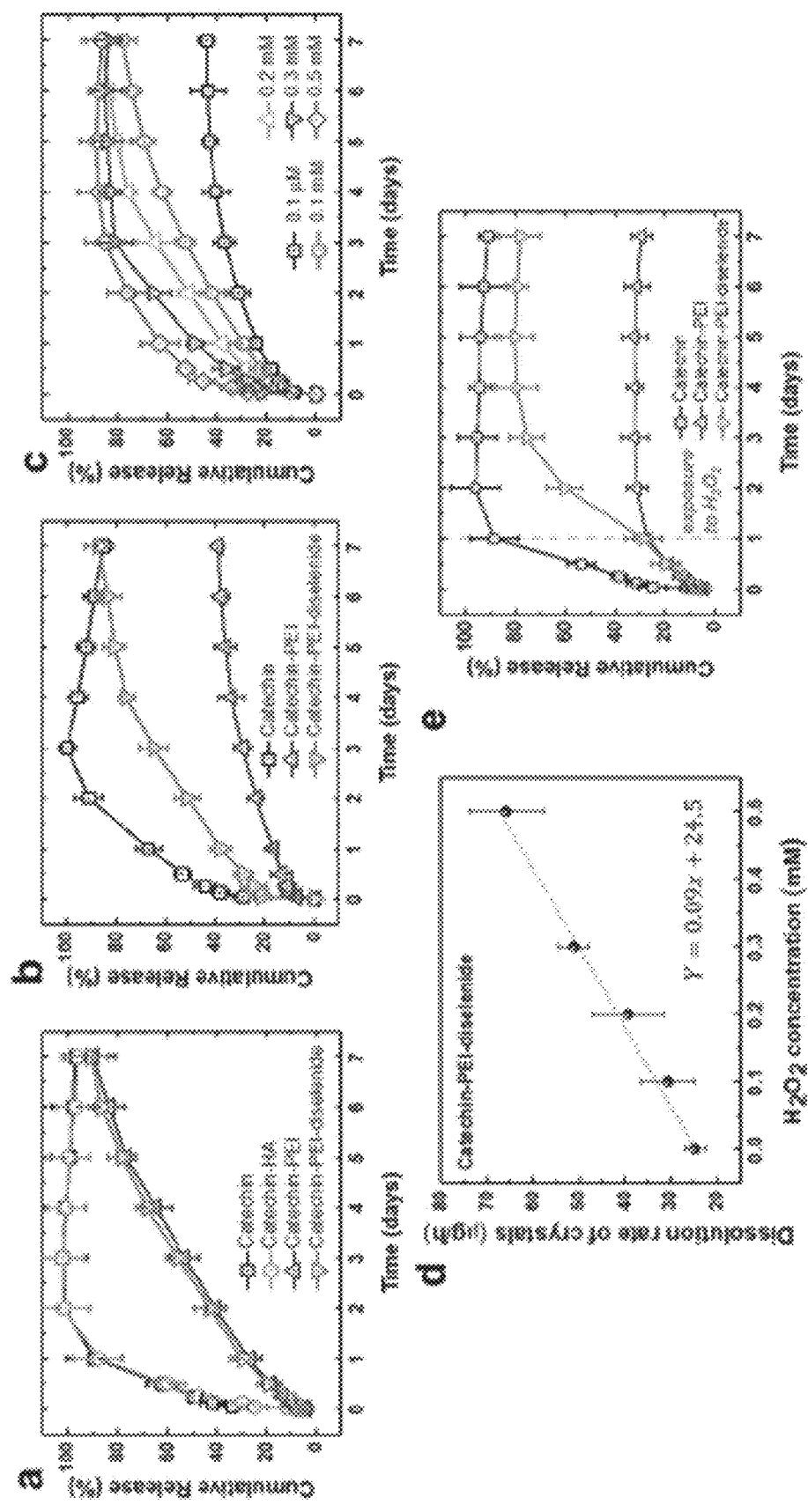
FIG. 5 shows cumulative release profiles of recrystallized catechin while incubated in (*a*) phosphate-buffered saline (PBS) or (*b*) PBS containing 0.2 mM $H_2O_2$; release profiles (*c*) and release rates (*d*) of catechin recrystallized with PEI-diselenide in PBS with different concentrations of H₂O₂; and (e) cumulative release profiles of recrystallized catechins when exposed to 0.2 mM H₂O₂ solution after one day.

Dissolution profiles of recrystallized catechin in phosphate-buffered saline are analyzed by measuring the amount of catechin dissolved and diffused from a dialysis membrane (FIG. 5a). Catechin crystals (25 mg) are placed in a dialysis tube (MWCO=500-1000 g/mol, Spectrum Labs) with PBS (1 mL). The dialysis tube is placed in the PBS media (499 mL) with different $H_2O_2$ concentrations (i.e., 0, 0.0001, 0.1, 0.2, 0.3, and 0.5 mM) and incubated at 37° C. under continuous shaking at 100 rpm. At designated times, dissolved catechin is collected and determined by reading the absorbance at 260 nm using a microplate spectrophotometer (Infinite 200 PRO, Tecan).

The pure catechin crystals dissolve rapidly and are quickly released through the dialysis membrane. Catechin recrystallized in the presence of HA does not exhibit a different hydrate form, morphology, or dissolution rate when compared with that of pure catechin crystals. Therefore, these crystals are not discussed further. In contrast, catechin recrystallized with PEI or PEI-diselenide demonstrates a slower release profile, each needing six days for the catechin crystals to dissolve completely.

In parallel, catechin crystals are incubated in PBS containing 0.2 mM of $H_2O_2$ (FIG. 5b). The overall dissolution rates of the pure catechin crystals and the catechin crystals complexed with PEI decrease in the media containing $H_2O_2$ as compared with the crystals incubated in PBS free of $H_2O_2$. This may be due to the decreased pH of the media containing $H_2O_2$ because the dissolution rate of catechin hydrate is known to depend on pH. Nevertheless, the PEI-free catechin crystal exhibits a faster dissolution rate than catechin complexed with PEI or PEI-diselenide, regardless of $H_2O_2$ concentration.

Interestingly, the catechin crystals prepared with the PEI-diselenide show a faster dissolution rate than catechin crystals prepared with only PEI in the media containing 0.2 mM $H_2O_2$. Eighty percent of the catechin complexed with PEI-diselenide dissolves continuously over 6 days. During the same period, only 30% of the catechin is released from crystals complexed with PEI. The increased dissolution rate suggests diselenide bond breaking triggered by $H_2O_2$.

The dissolution profiles of the catechin complexed with PEI-diselenide are further characterized with media containing different $H_2O_2$ concentrations (FIG. 5c). Increasing the $H_2O_2$ concentration from the normal physiological condition (0.1 µM) to pathological concentrations (up to 0.5 µM) leads to faster dissolution the of catechin crystals over the is 7-day test. The release rate, quantified from the slope of the catechin release curve (see FIG. 5d), is linearly related to $H_2O_2$ concentration.

Catechin crystals prepared with PEI-diselenide are also incubated in PBS over the first 24 h, followed by the addition of $H_2O_2$, to examine whether the crystals can adaptively expedite the dissolution rate. The final $H_2O_2$ concentration is 0.2 mM. Within the next 24 h, catechin is released actively as shown in FIG. 5e. The result confirms that the release profile of catechin crystals prepared using the PEI-diselenide can respond to an external oxidative stimulus. Therefore, this $H_2O_2$-responsive crystal may be able to circumvent side-effects that result from continuous passive dissolution of the antioxidant.

Dissolution Profiles from Diselenide-Crosslinked Hyaluronic Acid-G-Dopamine (HA-DOPA) Salts Our results also suggest that HA-DOPA would be a good fit with catechin. We also found that diselenide-crosslinked HA-DOPA has a desirable effect analogous to catechin/PEI systems when N-acetylcysteine (NAC) is the antioxidant.

Figure 6:
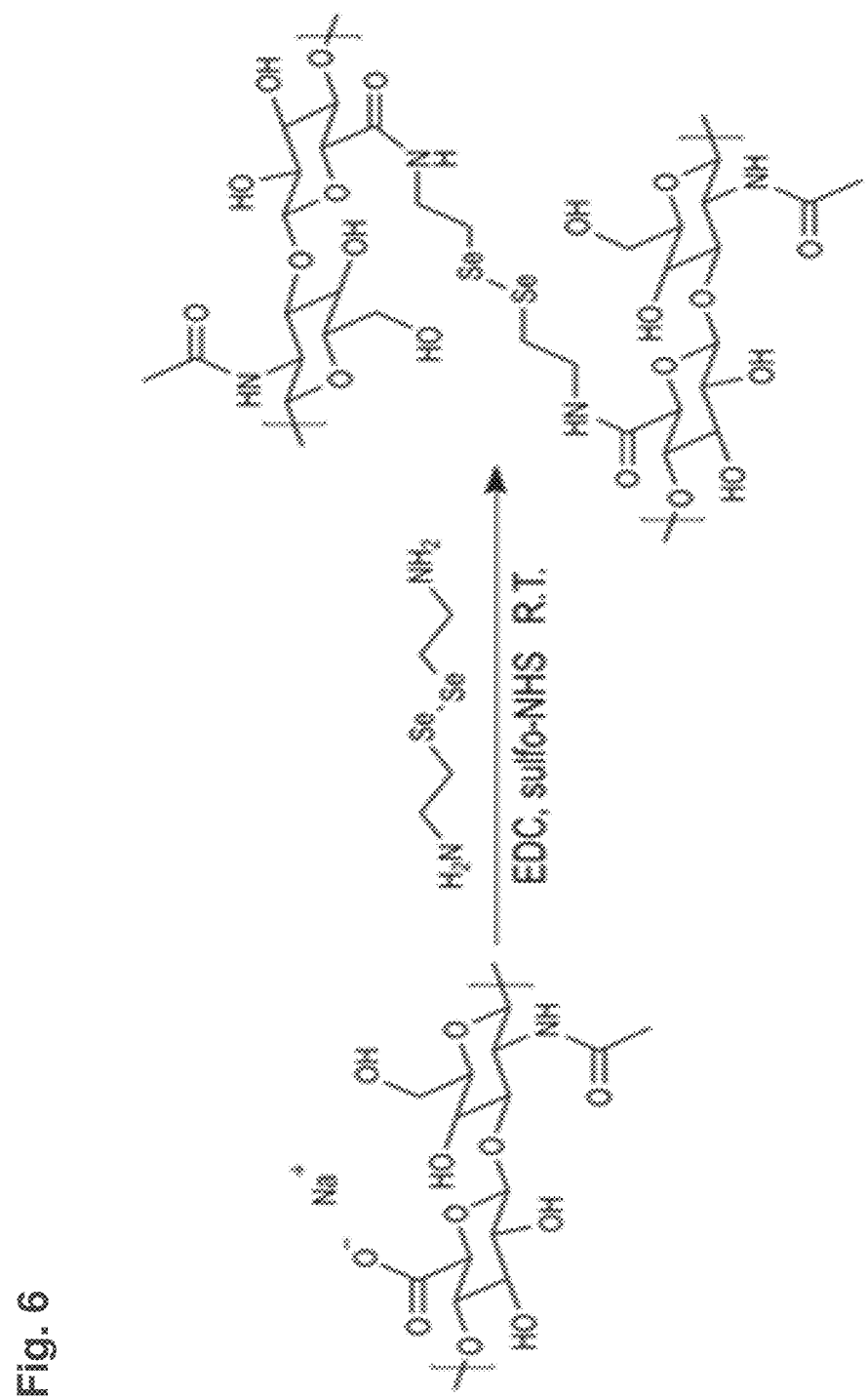
FIG. 6 shows a reaction scheme in which sodium hyaluronate reacts with selenocystamine to form an ROS-responsive polymer.

Sodium hyaluronate or the dopamine salt of hyaluronic acid (HA-DOPA) can be crosslinked by a reaction with selenocystamine (0.2 moles of selenocystamine per mole of HA glucoronic acid) at room temperature in the presence of ethylene dichloride (EDC) and N-hydroxysulfosuccinimide (sulfo-NHS) as shown for sodium hyaluronate in FIG. 6. The procedure described previously is used to recrystallize NAC in the presence of HA, HA-DOPA, or their diselenide-crosslinked analogs.

Figure 7:
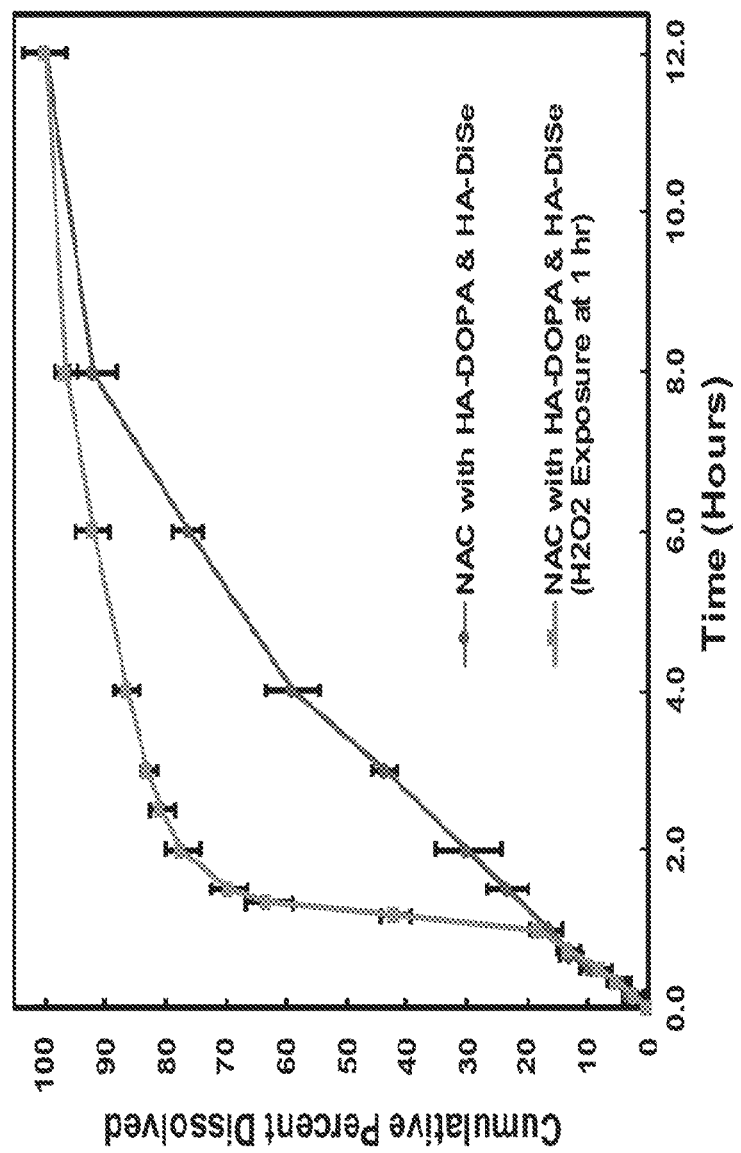
FIG. 7 shows extended dissolution profiles of N-acetylcysteine (NAC) crystallized with hyaluronic acid grafted with dopamine (HA-DOPA) or HA-DOPA crosslinked with selenocystamine (HA-DOPA-DiSe) and the effect of introducing hydrogen peroxide at the 1-h mark on dissolution of NAC from HA-DOPA-DiSe.

The extent to which $H_2O_2$ triggers the dissolution of NAC crystallized with HA-DOPA crosslinked by selenocystamine is examined, with some results shown in FIG. 7. The NAC concentration in PBS is monitored by measuring its UV absorbance at 320 nm. In $H_2O_2$-free media, NAC crystallized with crosslinked HA-DOPA shows an extended dissolution profile when compared with that of uncrosslinked HA-DOPA. Addition of 200 µM $H_2O_2$—a concentration considered to be pathologically oxidative in inflammatory tissues—triggers fast dissolution of NAC crystals. In contrast, NAC crystals prepared only with HA or HA-DOPA do not display the increased rate of NAC dissolution following the addition of 0.2 mM $H_2O_2$ solution.

The results demonstrate that polymers other than PEI can be used successfully to is produce an ROS-responsive antioxidant crystal, and that the choice of polymer will depend on the nature of the antioxidant with which it is crystallized.

The preceding examples are mere illustrations; the following claims define the inventive subject matter.

We claim:

1. A composition comprising an active oxygen-responsive antioxidant crystal, the crystal comprising:
   (a) an antioxidant; and
   (b) a disulfide- or diselenide-crosslinked polymer that is adsorbed onto a surface of the antioxidant;
   wherein the polymer, upon exposure to an active-oxygen stimulus, de-crosslinks to release the antioxidant from the composition in an amount effective to counteract the stimulus, and the composition comprises 1 to 20 wt. % of the disulfide- or diselenide-crosslinked polymer based on the combined amounts of antioxidant and disulfide- or diselenide-crosslinked polymer.

2. The composition of claim 1 wherein the antioxidant is water-soluble.

3. The composition of claim 1 wherein the antioxidant is a phenolic, a vitamin, or a carotenoid.

4. The composition of claim 3 wherein the antioxidant is a phenolic selected from the group consisting of phenolic acids, phenolate esters, flavonoids, and stilbenes.

5. The composition of claim 1 wherein the antioxidant is selected from the group consisting of p-coumaric acid, ferulic acid, ellagic acid, caffeic acid, gallic acid, hydroxybenzoic acids, flavonones, catechins, isoflavonoids, resveratrol, pterostilbene, lignans, apigenin, luteolin, tangertin, isorhamnetin, kaempferol, myrcetin, condensed tannins, quercetin, eriodictyol, hesperetin, naringenin, cyanidin, delphinidin, malvidin, pelargonidin, peonidin, petunidin, L-ascorbic acid, vitamin A, vitamin E, chromans, tocopherols, tocotrienols, beta-carotene, alpha-carotene, lycopene, lutein, zeaxanthin, N-acetylcysteine, glutathione, coenzyme Q10, melatonin, erythorbic acid, and lipoic acid.

6. The composition of claim 1 wherein the antioxidant is catechin, L-ascorbic acid, or N-acetylcysteine.

7. The composition of claim 1 wherein the polymer is water-soluble.

8. The composition of claim 1 wherein the polymer is selected from the group consisting of polyethylenimines, polyethylene glycols, polyglucosides, polysaccharides, hyaluronic acid polysaccharides, dopamine conjugates of polysaccharides, polyglycerols, hydroxyalkylcelluloses, polyvinyl acetates, polyvinyl alcohols, acrylic polymers, polyacrylamides, N-vinylpyrrolidone polymers, block copolymers thereof, and mixtures thereof.

9. The composition of claim 1 wherein the polymer is a diselenide-crosslinked, branched polyethylenimine.

10. The composition of claim 9 wherein the antioxidant is catechin.

11. The composition of claim 1 wherein the polymer is a diselenide-crosslinked hyaluronic acid grafted with dopamine (HA-DOPA) and the antioxidant is N-acetylcysteine.

12. The composition of claim 1 wherein the active-oxygen stimulus is selected from the group consisting of hydroxy radicals, hydrogen peroxide, superoxide anions, hypochlorous acid, peroxynitrite, and singlet oxygen-containing species.

13. A method which comprises crystallizing the antioxidant of claim 1 in the presence of a disulfide- or diselenide-crosslinked polymer to produce an active oxygen-responsive antioxidant crystal, wherein at least a portion of the polymer is adsorbed onto a surface of the antioxidant, and wherein upon exposure to an active-oxygen stimulus, the polymer can de-crosslink to release the antioxidant from the composition in an amount effective to counteract the stimulus.

14. The method of claim 13 wherein the antioxidant is selected from the group consisting of phenolics, vitamins, and carotenoids.

15. The method of claim 13 wherein the antioxidant is water-soluble.

16. The composition of claim 13 wherein the antioxidant is selected from the group consisting of p-coumaric acid, ferulic acid, ellagic acid, caffeic acid, gallic acid, hydroxybenzoic acids, flavonones, catechins, isoflavonoids, resveratrol, pterostilbene, lignans, apigenin, luteolin, tangertin, isorhamnetin, kaempferol, myrcetin, condensed tannins, quercetin, eriodictyol, hesperetin, naringenin, cyanidin, delphinidin, malvidin, pelargonidin, peonidin, petunidin, L-ascorbic acid, vitamin A, vitamin E, chromans, tocopherols, tocotrienols, beta-carotene, alpha-carotene, lycopene, lutein, zeaxanthin, N-acetylcysteine, glutathione, coenzyme Q10, melatonin, erythorbic acid, and lipoic acid.

17. The composition of claim 13 wherein the antioxidant is catechin, L-ascorbic acid, or N-acetylcysteine.

18. The method of claim 13 wherein the polymer is selected from the group consisting of polyethylenimines, polyethylene glycols, polyglucosides, polysaccharides, hyaluronic acid polysaccharides, dopamine conjugates of polysaccharides, polyglycerols, hydroxyalkylcelluloses, polyvinyl acetates, polyvinyl alcohols, acrylic polymers, polyacrylamides, N-vinyl pyrrolidone polymers, block copolymers thereof, and mixtures thereof.

19. A method which comprises controlling the dissolution rate, altering the crystallization behavior, or both, of the antioxidant of claim 1 by crystallizing the antioxidant in water in the presence of a disulfide- or diselenide-crosslinked polymer to produce a crystallized composition, wherein at least a portion of the polymer is adsorbed onto a surface of the antioxidant, and the antioxidant is water-soluble.

20. The method of claim 19 wherein upon exposure to an active-oxygen stimulus, the polymer can de-crosslink to release the antioxidant from the composition in an amount effective to counteract the stimulus.

\* \* \* \* \*